United States Patent [19]

Hutchinson

[11] Patent Number: 4,836,670
[45] Date of Patent: Jun. 6, 1989

[54] EYE MOVEMENT DETECTOR

[75] Inventor: Thomas E. Hutchinson, Ivy, Va.

[73] Assignee: Center for Innovative Technology, Herndon, Va.

[21] Appl. No.: 86,809

[22] Filed: Aug. 19, 1987

[51] Int. Cl.⁴ .............................................. A61B 3/14
[52] U.S. Cl. ..................................... 351/210; 354/62
[58] Field of Search ....................... 351/209, 210, 426; 354/62, 126

[56] References Cited

U.S. PATENT DOCUMENTS

| | | | |
|---|---|---|---|
| 3,986,030 | 10/1976 | Teltscher | 351/210 |
| 4,109,145 | 8/1978 | Graf. | |
| 4,595,990 | 6/1986 | Garwin et al. . | |
| 4,623,230 | 11/1986 | Weinblatt | 351/210 |
| 4,648,052 | 3/1987 | Friedman et al. | 351/210 |

OTHER PUBLICATIONS

By John Merchant, "Fixation Point Measurement by the Oculometer Technique", Optical Engineering, Jul.-/Aug. 1974, pp. 339-342, vol. 13, No. 4.
Behavior Research Methods & Instrumentation 1975, vol 7(5), pp. 397-429 "Survey of Eye Movement Recording Methods" by Laurence R. Young and David Sheena.
IEEE Transactions on Biomedical Engineering, vol. BME-21, No. 4, Jul. 1974, "Remote Measurement of Eye Direction Allowing Subject Motion Over One Cubic Foot of Space" by John Merchant et al., pp. 309-317.
Electrical and Electronic Engineering Department, University of Adelaide, "Eye Controlled and Other Fast Communicators for Speech Imparied and Physically Handicapped Persons" (Presented at the 22nd Conference on Physical Sciences and Engineering in Medicine and Biology Perth, 8/82, A. R. Downing Date Considered.
Comput. Biol. Med., vol. 14, No. 1, pp. 77-89, 1984, "Performance of an Eyetracker for Office Use", by James L. Levine.
Journal of the Optical Society of America, vol. 63, No. 8, Aug. 1973, "Accurate Two—Dimensional Eye Tracker using first and fourth Purkinje Images", by T. N. Cornsweet & H. D. Crane, pp. 921-928.

Primary Examiner—Rodney B. Bovernick
Assistant Examiner—P. M. Dzierzynski
Attorney, Agent, or Firm—Staas & Halsey

[57] ABSTRACT

A system for eye movement detection is disclosed that utilizes an infrared light emitting diode mounted coaxially in front of the lens of an infrared sensitive video camera for remotely making images of the eye of a computer operator. The reflected light causes bright eye effect which outlines the pupil as brighter than the rest of the eye and also causes an even brighter small glint from the surface of the cornea. The computer includes graphic processing which takes a video image, digitizes it into a matrix of pixels and analyzes the matrix. Using special algorithms the analysis determines the location of the pupil's center and the location of the glint relative to each other and with this information determines where the eye is gazing. If the eye-gaze is for a predetermined time at images in selected areas on the computer screen, the area is selected and results in actuation of other devices or the presentation of additional images on the screen. This is especially useable for handicapped persons to control their environment. Other uses include operator interfacing with workstations, cockpit controls and in industrial environments.

31 Claims, 10 Drawing Sheets

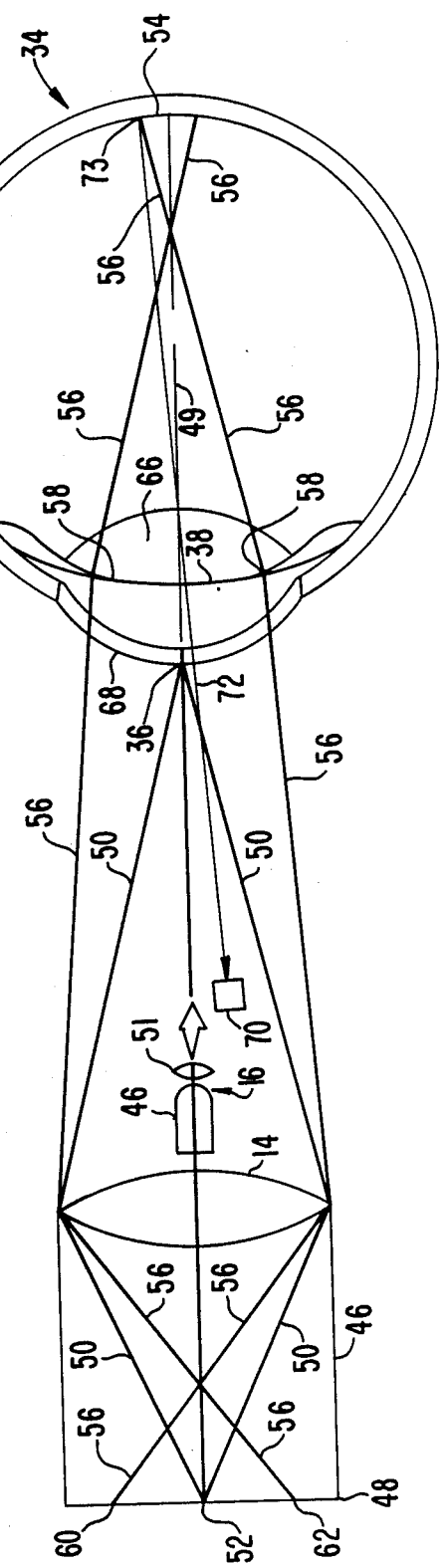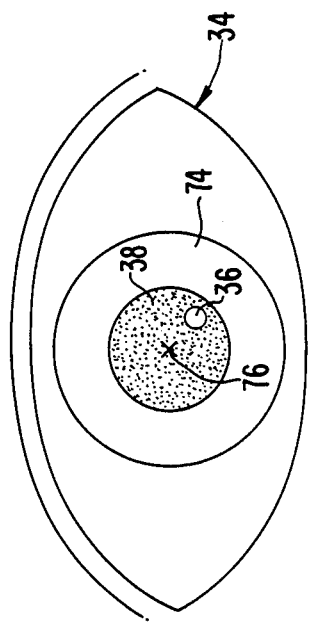
FIG. 3
FIG. 4

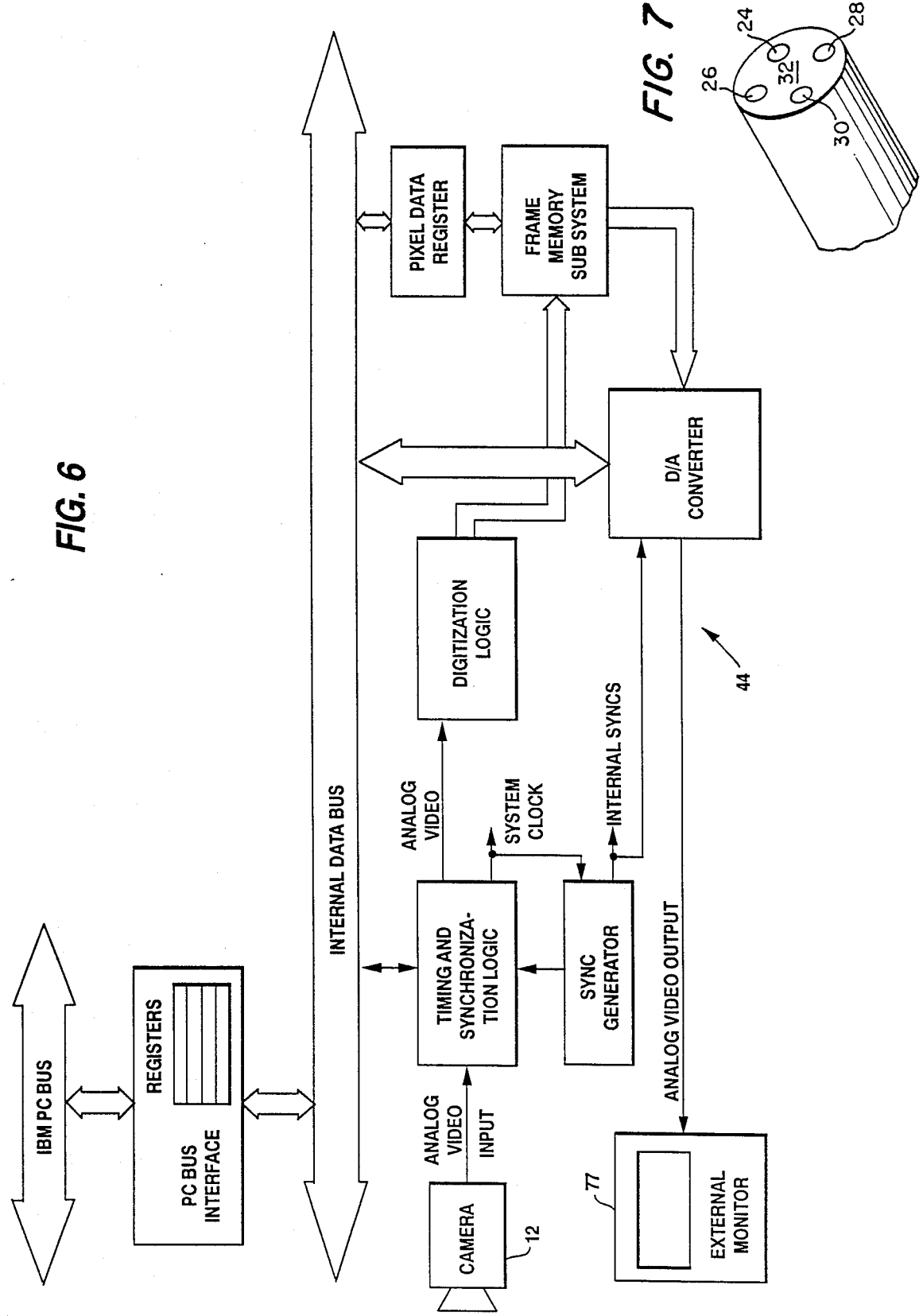

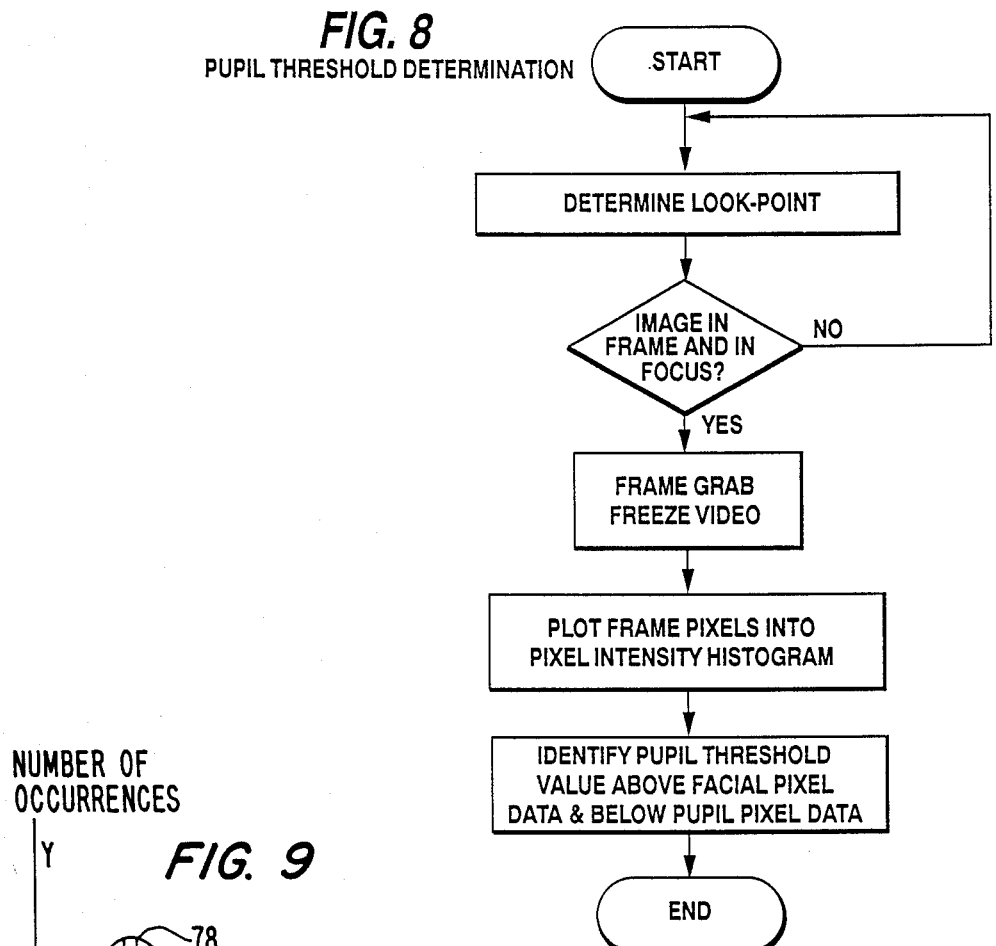
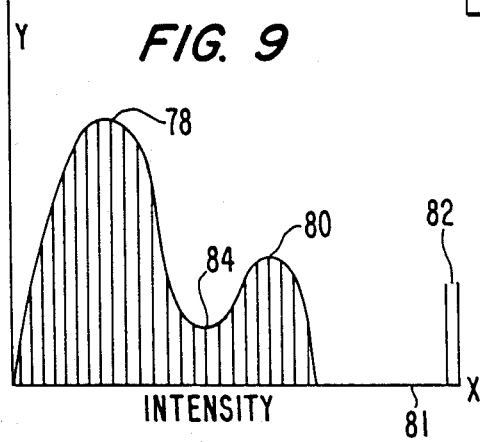
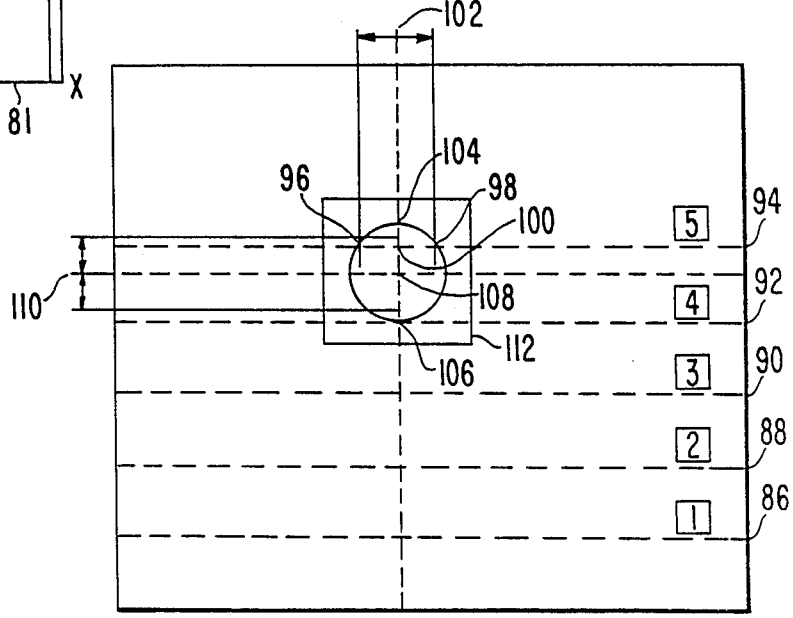

PUPIL-GLINT DISPLACEMENT MEASUREMENT

TWO POINT CALIBRATION

LOOK POINT DETERMINATION

DIRECTED AT
THE CAMERA

DIRECTLY ABOVE
CAMERA

TO THE LEFT
OF CAMERA

UP & LEFT

EYE MOVEMENT DETECTOR

This invention relates to an eye movement detector which is utilized as a means of interfacing an operator to a computer.

There are a number of eye movement detector techniques used in the prior art. Some of these have been applied to assist a handicapped person such as a quadraplegic who has lost many of his or her physical abilities and some have even lost the ability to speak clearly. Many of these severely handicapped people still have control of their eye movement and all of their mental faculties. So a device that they could control by eye movement alone which would help them control their environment, communicate messages, permit them to read and do other useful tasks would be a great boon and is very much needed. The eye movement detector should be relatively inexpensive, reliable, capable of expanded utilization, easily learned and easily used and otherwise be operator friendly. As used in this disclosure, the term "eye movement detector" means generically any technology relating to detecting either movement of the eye or detecting eye-gaze direction.

One of the eye movement technologies is electrooculography, which utilizes the difference in voltage existing between the cornea and the retina of the eye. Another technology is corneal reflection which utilizes the reflection of a beam of light from the various surfaces of the eye the beam crosses. The brightest reflection being at the outer corneal surface (first Purkinje image) with the second, third and fourth Purkinje images being dimmer and corresponding respectively to the inner surface of the cornea and the outer and the inner surfaces of the lens. Usually the reflection from the outer surface of the cornea and the inner surface of the lens are the two that are utilized.

A third technology is limbus tracking which detects a sharp boundary between the dark eyes and the white sclera (the limbus) which can be easily detected optically as to an indentifiable edge. A fourth technology is the use of a contact lens which rotates with the eye and is fitted with various devices to determine amount of the rotation. A fifth technique is to measure the ellipticity of the pupil which varies from circular as it is viewed head on to elliptical as it rotates away from the axis upon which it is viewed. A sixth technique is a movement measurement based on the head and eyes being moved together. A seventh technique is the oculometer which determines the center of the pupil and the corneal highlight from a reflected light and the change in the distance and direction between the two as the eye is rotated. There are additional techniques to those enumerated but these are some of the major ones. Some of them utilize a head or eye mounted device whereas others permit the eye motion detector to be mounted remote to the head.

The present invention is in a category of an oculometer eye measurement detector but some aspects of the invention can also be utilized with other techniques. The invention was primarily designed to be used by handicapped persons who need an eye movement detector type of device. When a healthy functioning person suddenly loses his ability to act for himself and to communicate, his mind becomes trapped within the body. The need to communicate and to control the environment becomes more acute for this individual who is left without motor functions and often without speech. It is a serious health problem nationally and one which is increasing. With the cost of keeping a severely handicapped person in an intensive care unit being extremely expensive, the eye motion detection system of the present invention can be paid for in a short period of time. While it is not expected to replace critical care for the severely disabled, it does mean a less intensive and less expensive form of care with large savings.

Complete motor dysfunction occurs as a result of both traumatic spinal injuries and gradual paralysis during the course of peripheral neuromuscular diseases. It affects young children growing up in mental and physical isolation without a way to educate their minds or acquire skills for adult life. It also affects adults who are accustomed to a normal life style and who must learn to cope with the resulting severe form of isolation from family, friends and others who must care for them.

The present invention was conceived as a means to prevent this isolation by allowing the individual to have control over the immediate environment and perform verbal or written communications. By using eye gaze alone, the system will allow the user to select certain tasks from a menu and then implement these tasks. A task is selected by gazing directly at the selected one of a multiplicity of tasks shown on the display screen while an infrared camera and infrared light monitor the eye position. A relatively inexpensive computer can recognize which one of the tasks the operator is gazing at and process the request. The image of the eye seen by the camera is actually a "bright eye" image similar to the pictures taken by flash illumination. This causes the pupil to appear light and provides a very high contrast image to permit accurate determination of the center thereof. The computer calculates the relative position of the center of the pupil and the light reflection or "glint" off the surface of the corneal bulge of the eye to determine where the eye is gazing.

Some aspects of the invention can be utilized with techniques other than the oculometer but this is the preferred one utilized in the present invention.

While the invention has been primarily developed for handicapped persons, the technology can also be used for industrial control, cockpit controls, workstation controls, and other applications where eye gaze control is desired. One such application is for emergency room personnel where both hands need to be utilized in treating the emergency but access to the computer by eye gaze would be helpful.

Some aspects of the invention are also utilizable for testing purposes based on eye movement.

The eye movement detector system is designed to permit activation of selected tasks from a display which functions as a computer control interface with the selection being made by eye gaze directed at a set of display driven menus in the form of icons, illustrations or boxes of written information. The device will implement user commanded changes of environment such as room lights, entertainment systems, access stored reading materials and so forth and call for help. It will also permit written communications for users without speech as well as verbal communications if enhanced with optional speech synthesizers.

The main components of the system include a solid state video camera sensitive to the near infrared with a manual 50 mm F1.4 lens and a coaxially mounted infrared light source. The camera is functionally coupled to an inexpensive computer system equipped with a color display as well as a suitable memory and input/output devices. Video images acquired of the eye by the vidoe camera are digitized by a suitable frame grabber or imaging board and the image processed by algorithms forming a part of the invention. A variety of output systems are provided including computer controlled AC power switches, video cassette recorders, television channel selectors and optional speech synthesizers.

The system can determine where a user is looking on a color display screen showing the menu selections and detect when the eye lingers for a predetermined period at any position provided by the menu. If the predetermined linger period is exceeded, it is as though a switch was closed for that special menu selection. The predetermined period for lingering can be varied from normally a half second to three seconds, but more commonly a two second period is utilized to produce the eye gaze response. The response is either to bring up another menu from the computer memory or if the lowest level menu selection has been made, to activate a device interface. Menus are organized by multilevel "tree" structure to prompt the user from the main menu until final selection of a response is made. Upon completion of this process, the main menu is redisplayed. The eye image is produced by illumination of the face with light from a near infrared light emitting diode source positioned out of focus at the center of the camera lens. This eye image is in the video frame image of one side of the face and consists of white and iris portions (dark), the back reflected infrared light out of the pupil (bright eye effect) and the corneal reflection of the source (glint). Eye gaze is computed at the relative x,y coordinates of the glint and the center of the pupil determined from the eye image using pattern recognition software. The bright eye effect provides a high contrast boundary at the pupil perimeter and a threshold between dark and bright eye intensities is relatively easy to distinguish.

Determination of the thresholds between the pupil and the surrounding eye portions and between the high intensity glint and surrounding eye portions is done with a histogram analysis of pixel intensities near the pupil and glint. The eye image region is identified within the overall frame image by a search for the maximum pixel intensity due to the corneal glint. The time to process several successive eye gazes is usually about one second. Minor head motions do not affect the relative glint and pupil positions as a function of eye gaze direction and therefore need not be compensated for.

The system interfaces with external applications specified within the menu set. Some of these include control of room lights and small appliances using widely available AC power controller systems. These systems interpret computer commands and turn on and off AC power through remote switching units. Other simple applications operate television channel advances with remote control, produces sentences from alphanumeric menu selections and may use a speech synthesizer to produce verbal communications. Another application is the read-a-book mode to provide the user reading material stored in computer files or retrieved from data bases over telephone modems.

The infrared source, preferrably an infrared light emitting diode, mounted coaxial with the video camera lens illuminates the user's face with near infrared light. This invisible illumination has a principle advantage of very little subject awareness of the monitoring process. Since the light is in coaxial alignment with the video camera lens, it results in light scattered back from the retina which effectively backlights a pupil so that it appears as a bright disk. This is the bright pupil or bright eye effect and provides a distinctive contrast to the rest of the eye and facial details. This greatly facilitates the determination of the periphery of the pupil so that the center of the pupil can be determined, which is one of the important points in the oculometer. An even brighter reflection is the surface reflection of the infrared light source from the corneal bulge which is the second important point utilized in the oculometer. The differential between the center of the pupil and the glint is measured by different x,y coordinates and is used to make the remote determination of where the eye is gazing. By using these two points which maintain their relative relationship during head movements while looking at the same location, the arrangement permits a reasonable degree of head movement. Since the illumination source and the optics of the video camera are coaxial, the image of the source always appears in line with the center of corneal curvature at least over the 25° of the cornea which can be considered as approximating a convex mirror. Thus the displacement of the corneal reflection from the observed pupil center is a function of eye rotation only.

Because of the physiological make up of the human eye, the eye normally will direct its gaze with a very high degree of accuracy at the gaze point. This is because the photo-receptors of the human retina are not uniformly distributed but instead show a pronounced density peak in a small region known as the fovea. In this region which subtends a visual angle of about 1°, the receptor density increases to about 10 times the average density. The nervous system aims to keep the image of the region of current interest centered accurately on the fovea as this gives the high resolution. The appearance of high resolution at all directions outside of this region is thus an illusion maintained by a combination of physiological mechanisms (rapid scanning with brief fixations), and psychological ones. As an example, a character on a typical computer display screen subtends an angle of about 0.3° at normal viewing distance. Such characters cannot be readily resolved unless the eye is quite accurately aligned and for a duration of about 0.2 seconds. The nominal curvature of the cornea for an adult human is approximately 8 mm radius on an eye of 13.3 mm radius. As with a convexed mirror, reflection of a bright object, such as the glint from the surface, forms a virtual image behind the surface which is one of the images detected by the video camera.

The pupil normally varies between 2 and 8 mm in diameter in adult humans. Although it is actually slightly elliptical in shape, as a practical matter it can be considered as a circle. The pupil appears elliptical when viewed other than along the optic axis. Because the radius of curvature of the cornea is less than that of the eye, the reflection upon its surface moves in the direction of the eye movement relative to the head. Since it only moves about half as far as the eye, it is displaced opposite to the eye movement relative to the optical axis or the center of the pupil. The differential displacement between the glint and the center of the pupil is used to determine the point of regard.

One of the advantages of the present invention is that it does not require any device to be fixed to the head and permits a relatively free natural head motion and yet still determines the point of regard or eye position.

Thus, the present invention determines eye gaze position using infrared light reflections from both the cornea and retina. A lens illuminates the user's face with near infrared light. A small fraction of the light entering the eye reflects back from the retina to the camera, creating an image that is the same phenomenon which causes the pink eye effect in photography where the flash bulb is located close to the optical axis of the camera. Basically it causes the pupil to be brighter than the remainder of the eye, whereas normally the pupil is darker than the remainder of the eye.

The cornea reflects an intense virtual image of the light emitting source and is referred to as the glint. The glint is sufficiently small that it is unnecessary to determine its center, although such could be done if desired. When a determination is made where the eye is looking, it is necessary to determine the center of the pupil. Usually the glint is located within the pupils image or along its outer circumference.

The computer has a frame grabbing image processing board that is commercially available which grabs a frame of the video camera pick-up of the eye as a $512 \times 480 \times 8$ bit frame. Pattern recognition software of the present invention calculates eye gaze direction by the determination of the distance and direction between the glint and the center of the pupil. In order to do this, the intensity thresholds between the pupil and surrounding portions of the eye and between the glint and surrounding portions of the eye are ascertained as a prelude to locating the center of the pupil and the location of the glint. A determination can then be made of the displacement measurements between the center of the pupil and the glint. A determination is also made in order to calibrate the eye movement detector with the individual. Then the algorithms in the invention utilize the foregoing information to determine actual gaze or look point.

The user is presented with a main menu which allows the selection of a type of application desired for implementation. A selection may be made of the environmental control, the personal needs, the word processing, entertainment games or the read text options in one arrangement. The selection is made by staring at the desired menu option for a total predetermined minimum time between ½ and 3 seconds. Beginning users would need the longer time whereas experienced users can operate satisfactory with the shorter times. Once a user's gaze is fixed an icon appears followed by an initial beep sound. The icon appears on the menu option most closely surrounding the user's gaze direction. If the user continues to look at this option, a second beep sounds and that option is selected. The first beep and icon feedback enable the user to change his selection or alter his eye gaze to abort a specific selection. All menus have a "backup" option which allows them to return to the previous menu in case a mistake is made.

The environmental control option allows the user to pick electrical devices in the surrounding area and alter them as desired. For example, the selection may be turn off the overhead light. In that instance the "lights" option on the highest level environmental control menu is selected. The next menu option allows the user to select the overhead light as opposed to other lights in the room. In the third level of menu the user gives the command to turn the light off. At the lowest level a prespecified code is sent to AC circuitry by readily available commercial control systems which triggers a specific appliance module for the overhead light. This is just one example of a number of menus that can be provided for the invention. For options which require more than a mere on/off signal, other remote controls suitable for a specific device may be provided.

The personal needs option allows the user to express the most common needs. This includes options which allow the user to call a nurse with a simple computer tone or by loud buzzer in the case of an urgent problem. Other menus could communicate being hungry, thirsty, cold or hot. A very important menu sequence shows that the patient has either a pain or itch and indicates a specific area of the body where the problem is located.

The word processing and communication mode includes options that enable the user to "get file" "print/voice", "exit", "save file", "write menu" and "clear text". The "write menu" option contains two rows of three menu sub-options which contain five clusters of alphanumeric symbols. When the user selects one of the clusters of letters, the next level menu contains each of the letters of that cluster divided into separate menu options. The user selects the desired letter and that letter appears in the text area placed in the lower third of the computer screen. Special sub-options are also included such as "punctuation", "delete letters", and "phrases". The "phrases" sub-option will call up another level menu that contains commonly used phrases which when selected are automatically typed on the screen.

The fourth application developed as an example of utilization of the invention is the read text application. This subprogram allows the user to select a text title, specific book, or New York Times article where the text has been previously stored either on a computer hard disk or available from a data base through a modem is accessed and displayed on the upper two-thirds of the screen. Across the bottom row the user has the option to turn to the next page, return to the previous page or exit the read text book subprogram. The user can thereby keep up with current event or be entertained or educated through books.

For a better understanding of the invention and its advantages reference should be made to the drawings which form a further part hereof and to the accompanying descriptive matter in which there is illustrated and described the preferred embodiment of the invention.

FIG. 3 is a schematic of the optical train used in the invention.

FIG. 4 is a schematic of the operator's eye showing the glint, pupil and iris.

FIG. 6 is a block diagram of some of the hardware used in the invention including the frame grabber.

FIG. 7 is a partial breakaway of the camera lens and illuminator of FIg. 1 modified to use four light emitting diodes.

FIG. 8 is a flowchart relating to pupil threshold determination.

FIG. 9 is a histogram showing the relationship of light intensity to number of occurrences.

FIG. 13 is a diagram representing the pupil-glint algorithm.

Figure 1:
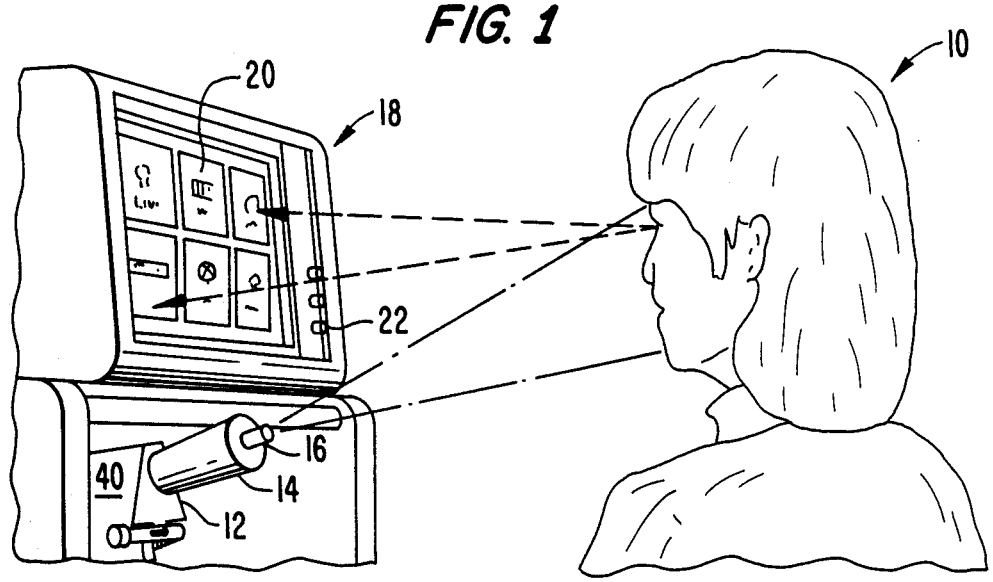
FIG. 1 is an illustration of the invention being used by an operator.

Referring to FIG. 1 there is shown an operator 10 utilizing the invention. The operator is shown sitting upright such as in a wheelchair but the operator could be laying down through other arrangements or through the use of mirrors in the arrangement shown. In the arrangement shown there is a camera 12, a camera lens 14 and an infrared illuminator 16. Mounted above the camera-lens-illuminator there is mounted a computer display 18 showing six pictures or icons 20. The display has the normal control knobs 22 for adjusting contrast and so forth. The operator is shown sitting upright such as in a wheelchair but could be laying down with a rearrangement of the invention or through the use of a mirror to permit the invention to be used while in the supine position. It should be noted in FIG. 1 that the camera-lens-illuminator is located below the computer display and approximately in the horizontal center thereof. Preferably this is 6 to 8 inches below the display and midway from the side thereof. This arrangement permits the eye to be illuminated and observed with minimum interference from the eyelid and eyelashes. The illumination is preferably by infrared light and FIG. 1 shows the light beam being shot into the eyes and the light reflecting back into the camera lens which through further processing as explained supra determines the position of the eyes and where they are looking. Staring at one of the areas if interest in the display or an icon or command displayed thereon usually from ½ to 3 seconds, depending on the arrangement in the computer and software and adjusted for the skill of the operator, automatically triggers the system as though the icon or area of interest or command displayed on the screen has a button pressed to close an electrical circuit.

It is to be especially noted as can be more clearly seen in FIG. 3 that the infrared illuminator and camera lens are coaxially mounted so that the illumination is along the same axis as the axis of the camera and its lens. This serves to outline the pupil of the eye by the bright eye effect so that it is brighter than the iris and is therefore easier to distinguish from the remaining parts of the eye. The glint from the surface of the cornea is also picked up and is a brighter image than the pupil.

An important feature of this invention is the coaxial mounting of the illuminator and the camera lens. In the past, arrangements of this kind have had the illuminator offset from the camera lens and folded to be coaxial by some type of optical device such as a half-silvered mirror or prism utilized in a beam splitting arrangement. The elimination of the need for a beam splitter results in a substantial improvement and simplication of the optical train.

Not shown in FIg. 1 is the closed circuit monitor for the camera which is useful in making and assuring that the eye is in focus or out of focus in the camera and whether the image of the eye inside this screen is drifting off to the right or to the left. While this extra monitor, in addition to the computer screen, is utilized in research, it is a distraction to the operator and the essential information from the monitor that is needed to stay in contact with the camera could be placed at the edge of the computer display. It is desirable that the operator pays attention to this computer display screen and not to the image being viewed by the camera on the monitor as that diverts the attention especially of a quadraplegic who has limited head motion.

The source of illumination is an infrared light emitting gallium arsenide diode of a kind readily available from many sources. They are approximately 2 to 3 mm in diameter and are normally used for communication purposes with a narrow light beam dispersion as opposed to some types which send light in all directions and are used mainly as indicator lights. They usually have a small built-in molded clear lens that condenses the light into a narrow beam. The one preferred emits light in the infrared region at 880 nanometers but others could also be used in the same range of approximately 900 nanometers such as one that emits light about 905 nanometers. A light emitting diode is preferred to a lasing diode which sometimes gives a speckle effect.

The preferred light should be invisible and of a sufficiently low intensity that it is perfectly safe for continued use by the operator. The near infrared wavelength of 880 nanometers has proven to be satisfactory for that purpose. Preferably, but not essentially, the light emitting diode (LED) is mounted at the base of a brass cylinder mounted coaxially near the front face of the camera lens which has at its open outer end (the one closest to the operator) a small focusing lens that supplements the lens on the LED so that the infrared illumination beam is a narrow beam directed to the eye and face of the operator so as to produce a better bright eye effect and better utilize the energy coming from the LED. Also, with the LED mounted in the brass cylinder, base any light from the LED will not leak out back into the camera lens, although this is not essential. The brass cylinder is mounted at the center of the camera lens with suitable wiring to supply the energy needs of the LED. It can be mounted to the center of a transparent disk on the front of the lens which disk maybe a haze filter which also protects the lens. The coaxial mounting of the LED illumination source with the lens of the camera provides for the illumination to go directly to the eye and return directly down the same path. This provides a bright eye effect which is often seen in flash shots in photography when the flashbulb is close to the optical center of the camera. The light enters the pupil and reflects off the retina in the back of the eye and back through the pupil again. This provides a high contrast image between the iris, which is around the pupil, and the pupil itself. Using the bright eye effect, the pupil boundary can be seen very clearly. The pupil itself is of a substantially brighter image than the surrounding eye whereas most other times the pupil appears to be the darker part of the eye since the illumination is from off the axis.

The lens used for the camera is a standard television camera 50 mm 1.4 lens with a diameter of approximately two inches.

Alternative arrangement for the illumination is shown in FIG. 7 where there is shown four LEDs 24, 26, 28 and 30 mounted on a transparent lens cover 32 on the front of lens 14. In this case the LEDs symmetrically surround the center of the lens and are offset from the center to part way towards the edge of the lens. They are pointed towards the operator but are not mounted in brass cylinders as mentioned earlier but do have the molded-in lens. They can still be considered coaxial and colinear with the lens of the camera as they are essentially near the same axis. The arrangement furnishes a less desirable alternative illumination of the operator's face but is possible for use as long as they are very near the axis. Although the light is not as intense, it is still useable. The illumination is largely in the form of a broken circle on the eye and face of the operator. The four LEDs are mounted in a circle equal distance from one another but half way from the center of the lens to its edges. It cannot be mounted further away from the center of the lens as a rapid falloff of the bright eye effect occurs. So the LEDs must be mounted substantially near the center or optical axis of the camera lens.

The single lens arrangement of FIG. 1 is still the preferred one and neither the arrangement of FIG. 1 or FIG. 7 interferes substantially with the picture of the eye being viewed by the camera and lens. The camera is chosen to be one that is sensitive to the infrared region of the light reflected from the eye and face. The one utilized is the Model TN2505A Solid State CID (Charge Injection Device) Surveillance Camera from General Electric Company, Electronics Par 7-G67, Syracuse, N.Y. 13221. The camera 12 is of a lightweight and small size and responds to very low light level in the infrared range of the illumination. It also responds to a full range of visible light which is unneeded by the invention and is filtered out by a filter mounted preferably at the rear of the camera lens to filter out any light below 800 nanometers. Other cameras or light sensors can be used as long as they are sensitive to the infrared region of the illumination at the light levels utilized.

The computer display 18 is a common colored display with the normal adjustment knobs 22 connected to a computer not shown in FIG. 1. The six screen area icons or controls 20 shown are represented of areas on the display more fully described elsewhere herein. While a normal color computer display of the cathode ray tube is used, other suitable displays may be used. It is to be noted that the eye movement detector of FIG. 1 has no attachment to the operators head but is remote thereto.

Usually the camera is between 60 and 80 centimeters from the head and mounted below the display observed by operator so that it is an underside shot of the face and eyes. This permits the camera to look up underneath the eyebrows and eyelashes and get a better and less obscured view of the eye. The arrangement provides approximately eight to ten inches of lateral movement of the eye and head but only approximately two inches in the z axis or movement to and from the camera. This can be increased with a greater depth of field of focus of the camera lens and illumination arrangement or by rapid automatic focusing of the lens.

Figure 1A:
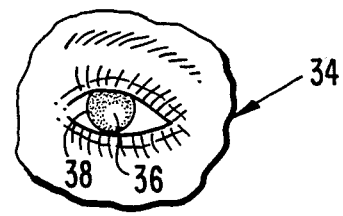
FIG. 1a is a breakaway of the operator's eye of FIG. 1 showing the glint and pupil.

FIG. 1A shows a breakaway view of the eye 34 of the operator 10 under infrared illumination which shows the glint 36 (slightly enlarged) and the pupil 38 under the bright eye effect.

Figure 2:
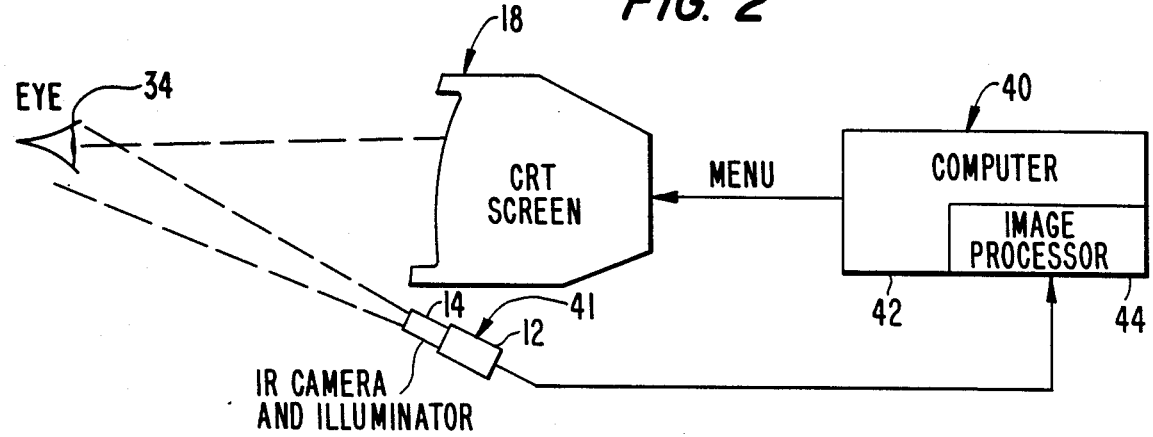
FIG. 2 is a schematic of the arrangement of the equipment used in the system.

FIG. 2 shows a schematic of the arrangement of the equipment used in the system and shows the eye 34 viewing the computer display or cathode ray tube (CRT) screen 18 under the illumination of infrared (IR) camera in illuminator assembly 41. The assembly consists of infrared camera 12 and the lens 14 which has on its front the LED illuminator arrangement, not specifically shown in FIG. 2. Connected to the camera is a computer and image processor assembly 40 consisting of a computer 42 an an image processor 44, all of which will be more fully described in connection with FIGS. 5 and 6. The computer supplies the menu of scenes or icons or controls to the CRT screen which is approximately 8½ × 10 inches in size. The display could be a flat panel display rather than a cathode ray tube so long as it properly interfaces with the computer and provides at the proper speed computer generated scenes or icons or controls.

In FIG. 3 there is shown a schematic of the optical train used in the invention. The operator's eye 34 is in cross-section to the right and the camera and illuminator are to the left. The inside of the camera 46 has to its left the film or focal plane 48 and on the front the lens 14. Behind the lens 14 is a filter (not shown) for filtering out light below 800 nanometers. This filter could also be in front of the lens. In the front of the lens and to its center is the illuminator 16 which is an infrared light emitting diode 51 with the diode portion to the left and a molded lens in the shape of a rounded nose to the right. In front of the lens is another lens 51 to further condense the illumination from the LED to direct a parallel beam of infrared light to the eye in the direction of the arrow. In the figure the camera and illuminator are mounted coaxial with the optical axis 49 of the eye. A first reflection from the illuminator is the glint 36 and the retrace of the reflection is backward along glint ray trace lines 50 so as to focus at 52 in the focal plane 48 of the camera. The illumination from the LED that passes through the eye and reflected off of the retina 54 is defined by pupil ray trace 56. As the reflection from the rear of the retina passes through the pupil 38 and is condensed on the focal plane 48 of the camera between 60 and 62 it outlines the outer periphery 58. This gives the diameter of the pupil as seen by the camera sensor. Also shown in FIG. 3 is the eye lens 66 and eye cornea 68. It can be seen that the eye cornea or corneal bulge 68 is of a different spherical diameter than the eyeball itself. The true gaze point 70 lie on the gaze point axis 72 which intersects the rear wall of the eye at the fovea centralis (usually referred to in the shortened version as "fovea") a small depression in the macula lutea of the retina. The macula lutea is usually referred to in the shortened version as the "macula" and is the area of the eye near the center of the retina but slightly off axis in which visual perception is most acute. The center of the macula is approximately 3° to 6° off of the optical axis of the eye.

With reference to FIG. 4 which is a schematic version of FIG. 3, there is shown operators eye 34 with the pupil 38 surrounded by the iris 74. A cross 76 indicates the center of the pupil. The glint is shown off the center at 36. The separation between the center of the pupil and the glint is utilized in the invention to show where the eye is looking.

Figure 5:
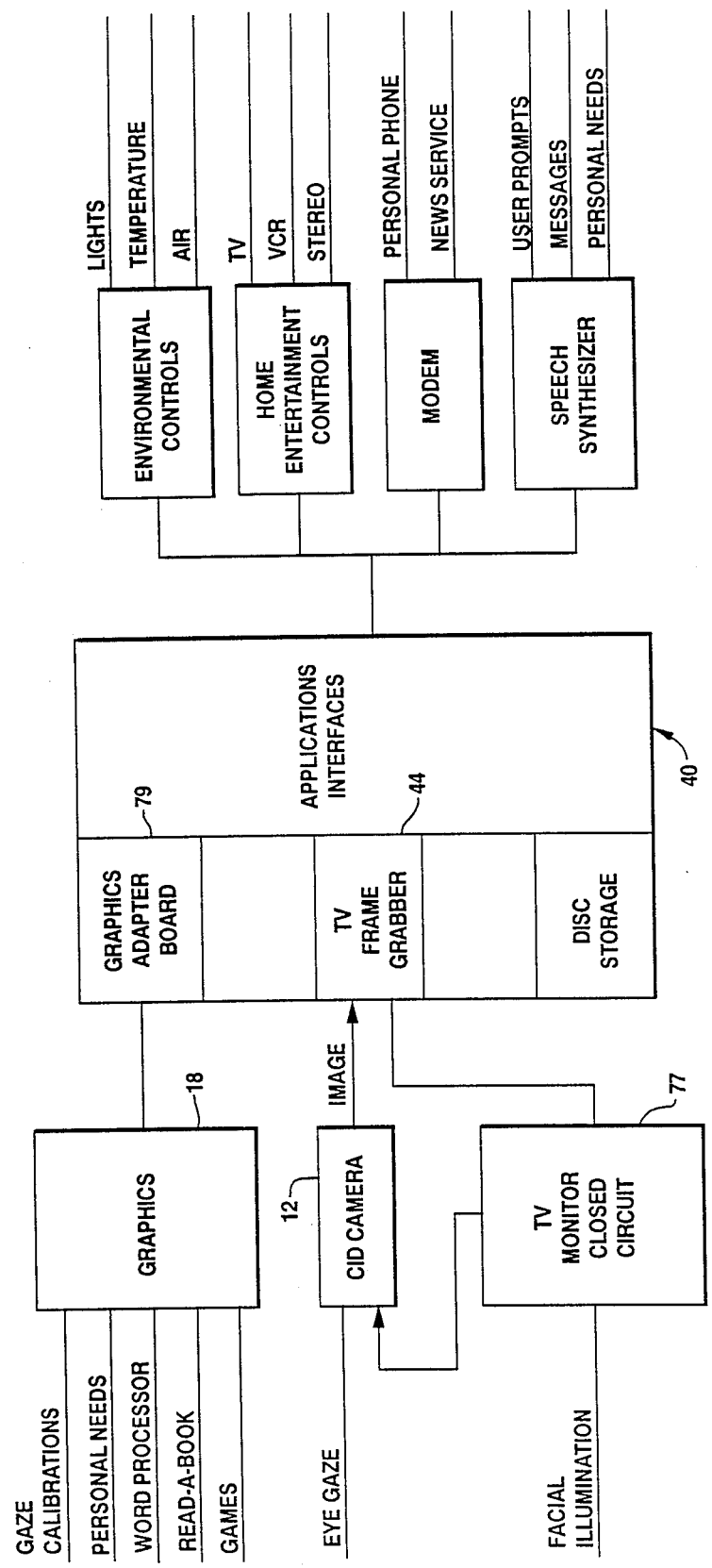
FIG. 5 is an overall block diagram of some of the software and hardware utilizable in the invention.

The reference to FIG. 5 there is shown an overall block diagram of some of the software and hardware utilizable in the invention. In the center section is shown a computer and image processing assembly 40 which contains the image processor or TV frame grabber 44 as well as the computer which is not specifically delineated. The computer is preferably an IBM PC/XT which is available from the International Business Machines Corporation in Armonk, N.Y. There are numerous computers of a similar nature available from many sources that could likewise be utilized. The computer is populated with 256K of dynamic random access semiconductor memory and a 10 megabyte of hard disk storage. The graphics and control files are stored on this disk. A TV frame grabber or image processor circuit board 44 is placed into the assembly. The one preferred is PCVISION (Trademark) Frame grabber available from Imaging Technology, Inc., 600 West Cummings Park, Woburn, Mass. 01801. The frame grabber is more fully described in connection with FIG. 6 below.

Facial illumination is supplied to the operator face by the infrared source previously described and photographed by the previously described CID videocamera 12. The eye gaze is picked up by the camera which shows in real time on the TV monitor 77, which is a closed circuit with the camera, the image being picked up by the CID camera. Also the image is being fed in real time to the TV frame grabber which grabs frames as desired and will be explained more fully below. The computer also contains a graphics adapter board 79 for interfacing with the graphics display 18 from the computer. Appearing on this computer display 18 are graphics 20 as needed. These graphics or icons or controls include the various menu selections for personal needs, word processing, read-a-book, games as well as other menus which may be developed.

As shown, there are four major types of applications. They are the environmental control, the home entertainment controls, the modem and the speech synthesizer. Others can be added and all interface through the applications interfaces.

The environmental controls can control the lights, temperature and air and other desired environmental controls. The home entertainment controls can control the TV, video cassette recorder (VCR), stereo or other desired entertainment features. The modem interfaces for personal phone calls, news services and other data bases over the phone system. The speech synthesizer can furnish user prompts, messages, personal needs and other functions such as calling the nurse as desired.

While FIG. 5 shows both a TV monitor 77 and graphics display 18, a preferred alternative is for the essential information shown by the TV monitor 77 to be shown at the periphery of the graphics display 18 so that a separate TV monitor would not be necessary.

With reference to FIG. 6 there is shown, a block diagram of some of the hardware used in the invention with specific emphasis on the image processor or TV frame grabber 44. This is a sub-system which is used to obtain digitized video frames from the camera and has its own memory. The frame grabber is in the form of a circuit board that can be inserted into an expansion slot of the IBM PC/XT host computer. A number of such frame grabber boards are available that are capable of use and the description that follows is of the commercial board PCVISION (trademark) used with the present invention. The description is for illustrative purposes only as the technology is generally known. The analog video signal from the camera is inputted into the timing and synchronization logic function which then sends an analog video output signal to digitization logic where the signal is digitized by an analog to digital (A/D) converter that samples at discrete time intervals and digitizes the analog video signal. The digitized output is binary and is sent to the frame memory sub-system where one pixel is stored in each of the memory locations and the storage is organized somewhat like the original camera target except they are digital pixels. This digital information can be sent to the pixel data register and accessed by the host computer through the internal data bus.

The host computer is attached to the internal data bus through the personal computer (PC) bus interface which contains a member of registers which are controlled registers which control the PCVISION (trademark) frame grabber by the host computer.

The camera information (images) is run as a closed circuit that is constantly monitored by the monitor. A digital representation of the images is available on-demand for the computer to analyze. This on-demand is referred to as frame grabbing since one of the images or fames is grabbed for computer analysis as the various frames continuously go by on their way through the loop from the camera to the monitor. A particular frame grabbed maps 64 kilobytes of its frame memory into the memory space of the host computer. Since there is a total of 256 kilobytes of frame memory on the grabbed frame, only $\frac{1}{4}$ of the frame memory is accessible to the host computer at any time.

The video source for the frame grabber is a standard RS-170 signal. It is composed of analog video information and timing information. The timing information is present between each horizontal scan line. The RS-170 video standard employs an interlacing scheme for displaying as much information as possible in a flicker free manner. With interlacing, the horizontal scan lines of the complete image (called a frame) are divided into two groups called fields. The even field consist of the zeroth (top most), second, fourth and all following even numbered scan lines in the frame. The odd field consist of the first, third, fifth and all remaining odd numbered lines.

When displaying a video image all lines of even field are transmitted in succession, followed by all lines of the odd field with the sequence repeating continuously. The frame grabber acquires and stores an image so that the lines from a pair of successive odd and even fields are merged properly in the frame memory. Even field lines are at even y locations and odd field lines are at odd y locations in the frame memory.

The system timing and synchronization is accomplished by the timing and synchronization and by the system clock. Timing can be extracted from the video signal by a sync stripper which is then passed to a phase locked loop that locks the internal timing of the frame grabber to the video source. If the video signal is lost, the frame grabber automatically switches timing to an internal crystal to avoid the loss of any image data.

The digitization logic is a digital-to-analog converter which converts the analog video signal into a series of digital values, or pixels. This is accomplished by sampling the analog signals at discrete time intervals and converting each individual sample to a digital value. The frame grabber samples the analog signal 10,000,000 times per second. This results in 512 pixels for each horizontal line of the image. The RS-170 standard results in 480 lines of digitized information per frame.

The actual process is accomplished with a flash analog-to-digital converter. The frame grabber digitizes to an accuracy of 6 bits per pixel. Therefore, a maximum of 64 gray levels are possible for each pixel.

The frame grabber memory is organized as an array of 512×512 pixels and provides four bits per pixel. In this configuration, the most significant four bits of the analog-to-digital converter output are stored in the frame memory.

The frame memory is mapped in 64 kilobyte blocks into the memory space of the host computer for direct read/write access. Each of the four 64 kilobytes can be selected individually for direct mapping. The four blocks represent the four quadrants of the frame. By different arrangements, all the quadrants could be simultaneously accessed and future embodiments of the invention may provide for this. The upper right quadrant of the picture from the video camera is usually utilized and must contain the image of the pupil.

The frame memory subsystem simultaneously acquires and displays an image in the monitor. This is accomplished with a read/modify/write cycle on each frame memory. The pixel which is read is transmitted to the display logic for digital-to-analog conversion, and the new pixel from the digitizing logic is written into the memory. Therefore, a one frame lag exists (1/30 of a second) when the frame grabber is simultaneously acquiring and displaying an image.

In reading and writing the frame memory, the memory is accessed by the host computer through the but interface. The 512×512 frame memory is divided into four equally sized segments or blocks which are quadrants of the frame or image. Using one of the registers of the PC Bus Interface, which interfaces the internal data bus with the frame memory subsystem, each of the four segments can be multiplexed into the memory space of the host computer. This is done to limit the amount of host computer address space required by the frame grabber, while maximizing the transfer rate from the frame memory to the host computer memory.

Each pixel in the selected quadrant is individually accessed through the PC Bus Interface. When data is read from or written to the frame memory, the Pixel Data Register is updated.

The digital-to-analog (D/A) converter changes the digitized information or image back to an analog format for display on the external monitor.

The SYNC generator generates internal synchronization signals for the frame grabber. Two signals from a sync generator, an internal composite sync and an internal composite blank are input to the digital-to-analog computer. The D/A converter uses the signals to reconstruct an RS-170 signal for input to the external monitor.

The 64 kilobyte of digitized graphics information grabbed by the host computer is analyzed by software in a manner described below.

With reference to FIGS. 8 and 9, it is first necessary in the gaze point algorithms utilized with the invention to determine the pupil threshold intensity and the glint threshold intensity. These are the intensities of reflected light which are determined that a pixel in a digitized frame that has been grabbed of the eye has an intensity, respectively, just below the intensity of the pupil and just below the intensity of the glint. As stated earlier, by utilizing the illumination source mounted coaxially with the camera the pupil has a higher intensity than any other part of the face and eye except for the small glint which has the greatest intensity of all.

The flowchart of FIG. 8 represents the manner by which the pupil threshold determination and the glint threshold determination is made. This is also represented by the histogram of FIG. 9 which results from the flowchart.

First, it is determined that the look point is such that the eye is in the quadrant of the frame of the camera that will be examined and the image is in the frame. If it is determined that the eye is not in the frame and in focus, another look point is obtained and a determination made of focus and presence. If the image or eye is in the frame and in focus, the frame is grabbed to freeze the video frame in digitized form for processing by the computer as described earlier.

The frame that is grabbed is plotted as to the intensity of each individual pixel into a pixel intensity histogram. This is best seen in FIG. 9 where the intensity of the light of each pixel is on the x axis and the number of occurrences at that intensity is on the y axis. The histogram actually represents a pictorial representation of the data. The data is not actually plotted to obtain a determination but merely is used to illustrate what the data looks like. It can be seen from FIG. 9 the largest amount of data or frequency of occurrences is represented by the lower intensity hump 78 and a smaller amount of data is represented by a higher intensity hump 80. Between the two humps is a low point 84 which is the pupil threshold value that represents an intensity above the facial pixel intensity data and below the pupil pixel intensity data. As seen on the histogram, there are very high intensity pixels 82 of which there are only a few occcurences. This represents the high intensity glint and between the pupil intensity and glint intensity is the determined glint threshold intensity 81. The pupil threshold determination 84 then is the minimum number of occurrences between the two bands represented by the first hump, mostly facial data and the second hump representing the pupil. It is a value above the facial pixel intensity data and below the pupil pixel intensity data. Once the pupil threshold value is determined and the glint value (not specifically shown on flowchart) is determined or identified, the flowchart of FIG. 8 has been completed. The entire process of determining the pupil threshold is done in a fraction of a second by the computer using this algorithm.

Figure 10A:
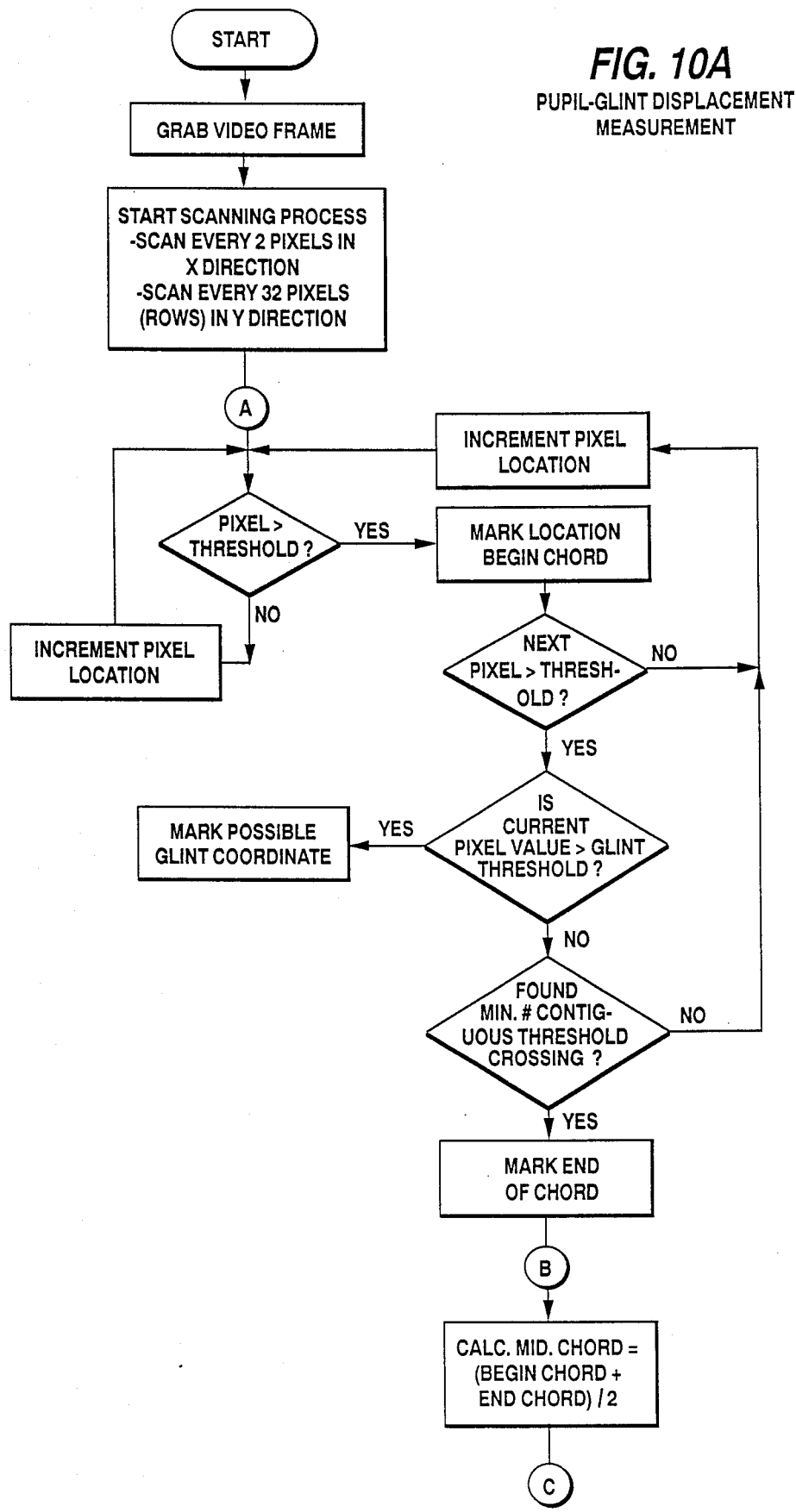
FIGS. 10A and 10B are flowcharts relating to pupil-glint displacement movement.
Figure 10B:
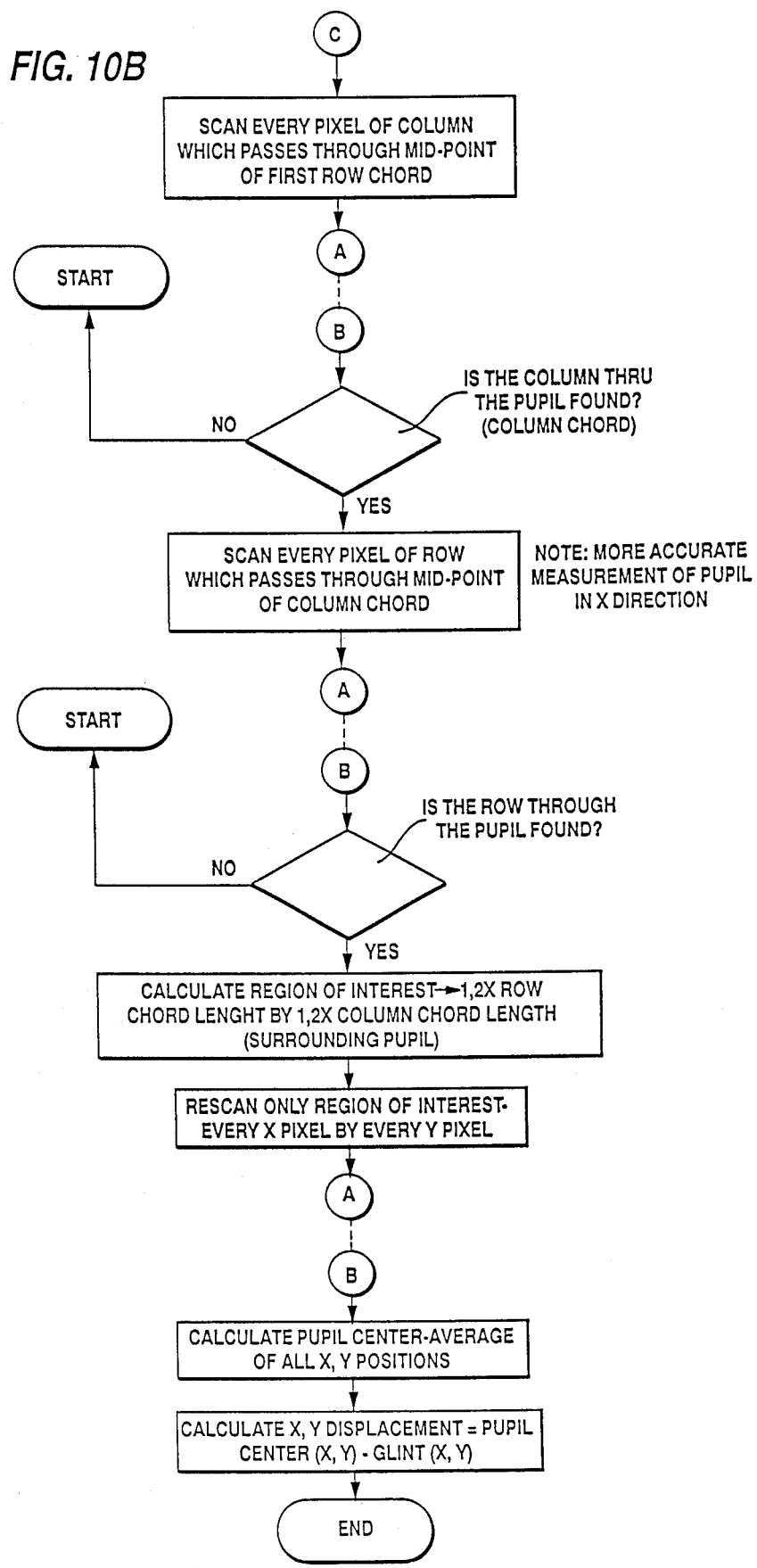

References now made to FIGS. 10A and 10B which is the flowchart showing the determination of the pupil glint displacement measurement which is basically a forecast algorithm. First, a video frame is grabbed showing the eye to be analyzed. The frame is searched very quickly to define the pupil feature. This is done by searching ever two pixels in the x direction and scanning every 32 pixels in the rose or y direction.

The reason the scan is in fine resolution in the x direction and coarse resolution in the y direction is because first an effort is made to find a suitable row chord which is the x or horizontal direction. Then the vertical chord passing through the midpoint of that horizontal chord is examined pixel by pixel in a vertical direction and the portion laying in the pupil is a first approximation of the vertical diameter of the pupil. The midpoint of this first approximate diameter is then determined and the horizontal chord passing through this midpoint is examined pixel by pixel which represents the first approximate horizontal diameter of the pupil being that portion laying within the pupil's perimeter. Of course, this scan strategy could be changed to where the defined resolution is in the y mode and the coarse resolution is in the x mode and the column or vertical cords are scanned first.

With further reference to FIG. 10A the "A" and "B" represents a portion of the flowchart where the steps between "A" and "B" will be repeated. Also the "C" in FIGS. 10A and 10B show where they are to be joined.

Starting with "A" a pixel is compared to the pupil threshold intensity determination made earlier and if it is less value than that threshold, it is a No and the scan is incremented to the next pixel location and again the question of whether the pixel is greater than the threshold or not is determined. If the answer is again No, the scan is incremented to the next pixel location and the question is again asked. This is repeated until a pixel is found whose intensity is greater than the threshold level. When the answer to the question is Yes, that location is marked as the possible beginning of the chord. And the next pixel is examined and if the question as to whether the pixel intensity is greater than the pupil intensity level is asked. If the answer is No, the scan is incremented to the next pixel location in the procedure that started with "A" where the process is begun again. However, if the answer to the question is the current pixel value is greater than the last pixel value (Yes) then the question is asked is the value greater than the glint threshold. If the answer is Yes, then it is marked as a possible glint coordinate. Please note that the glint is small enough that no effort is made to find its center although such could be done if desired. The glint location is used by itself as the coordinate. If the current pixel value is not greater than the glint threshold intensity value, the answer to the question is No.

The next question is whether a minimum number of contiguous pixels whose value has crossed the pupil threshold been found. If the answer is No, then the scan is incremented to the next pixel location and the procedure is begun again at "A". If the answer to the question is Yes, then that pixel is marked as an end of the chord and the procedure between "A" and "B" have ended. The minimum number of contiguous pixels having a value greater than the threshold value is a program variable but the preferred number is usually 18. This only refers to every other pixel in a horizontal scan since only 1 in 2 are being scanned on the horizontal and 1 horizontal row out of 32. The entire frame of pixels is a matrix of 256×256 pixels.

The next step is to determine the middle of the horizontal chord. This is done by calculating the middle of the chord by adding the location of the beginning of the chord which has been marked to the location of the end of the chord which has been marked and dividing this length by two. The next step is to scan every pixel of the vertical column of pixels which passes through the midpoint of the first row chord using the steps between "A" and "B". Is the column through the pupil found, that is the column chord? If the answer is No, then the procedures outlined in the flow chart are started at the beginning. If the answer is Yes, then the vertical or column chord has its midpoint determined and every pixel of the horizontal row of pixels which passes through the midpoint of the column chord is scanned. It should be noted that the original scan of the horizontal first chord was every other pixel. Now it is more accurate measurement by scanning every single pixel. The scanning procedure is a repeat of the steps between "A" and "B" and then the question is asked is the row through the pupil found. An if the answer to the question is No, the steps in the flow chart are started from the beginning again. If the answer is Yes, then this is the determination that the horizontal diameter chord and vertical diameter chord has been found and the region of interest is calculated as being 1.2 times the row chord length by 1.2 times the column chord length surrounding the pupil. In other words, a square surrounding the pupil of 1.2× the diameter pupil with the pupil at the center is chosen as the region of interest.

The next step is to scan every single pixel in this region of interest in the x direction and y direction. This scan is carried out by repeating the steps between "A" and "B" with results that the pupil center is a calculated average of all the x,y positions that determine the beginning and end of a chord through the pupil. The glint has been marked in carrying out the steps between "A" and "B" with its x,y position being found at the same time. The next step is to calculate the x,y displacement or differential between the glint and the center of the pupil. This is equal to the x,y of the pupil center minus the x,y of the glint. This is the end of the pupil-glint displacement measurement flow chart procedure.

Since the important value to determine where the eye is gazing or looking is the differential or displacement both as to direction and distance between the pupil center and the glint, the information has now been found to enable such eye gaze direction to be determined.

With reference to FIG. 13, there is shown a square representing 256×256 pixels that are digitized from a frame grabbed by the video camera and present in the computer for analysis. A first horizontal scan 86 is made of every two pixels in the row. This first scan is 32 pixels from the bottom of the matrix and the intensity of each pixel is compared with the pupil threshold previously determined in order to find whether the scan is passing through the more intense light of the pupil or not. Obviously, the first scan did not pass through the pupil so a second horizontal scan 80 is made of every pixel. And since again this scan did not pass through the pupil a third horizontal scan 90 is made of every other pixel. Both the second scan and third scan are 32 pixels higher in a vertical direction since again the pupil was not intersected. The fourth horizontal scan 92 is 32 pixel higher on the matrix and is made of every other pixel. However, the pupil chord of the fourth scan barely touches the pupil area and by designation the length within the pupil must be at least 18 pixels long of every other pixel before a preliminary determination that a horizontal chord of the pupil has been found. The 18 pixels is used as a satisfactory minimum length, but other lengths could be chosen.

Since the forth horizontal scan did not meet the minimum length requirement, a fifth horizontal scan 94, 32 pixels higher on the maxtrix, is made. This time a pupil chord exceeding the minimum length of 18 pixels is found, so the next step of determining the center of this horizontal chord is made. It is known from the fifth horizontal scan the left edge 96 and the right edge 98 a horizontal pupil chord has been found. It is then a simple matter of determining the mid-point 100 of the chord between the left 96 and right 98 edge of the pupil. Then the vertical column 102 that intersects this midpoint 100 is scanned at every pixel provided this vertical chord exceeds the minimum length of 18 pixels. The analysis proceeds if it is of minimum length but if it is not, the search is aborted and a new frame is grabbed for analysis. Assuming the vertical chord exceeds the minimum length then a determination of the center of that vertical column chord is made between where it intersects the upper edge of the pupil at 104 and the lower edge of the pupil at 106. This is the midpoint 108. This forms a first approximate vertical diameter of the pupil.

The horizontal row 110 that intersects the midpoint of the pupil 108 on the vertical column is scanned at every pixel. From this information the center of the horizontal chord of the pupil is and should approximate the midpoint 108 of the vertical column chord 102.

The next step is to expand the region of interest around the pupil by multiplying the vertical chord of the pupil aligned with vertical column 102 and the horizontal chord aligning with horizontal chord 110 (both of which cords are diameters of the pupil) and multiply these lengths by 1.2. This is represented by the square 112 shown in FIG. 13. Also, the detailed matrix of this region of interest is better seen in FIG. 14.

Figure 14:
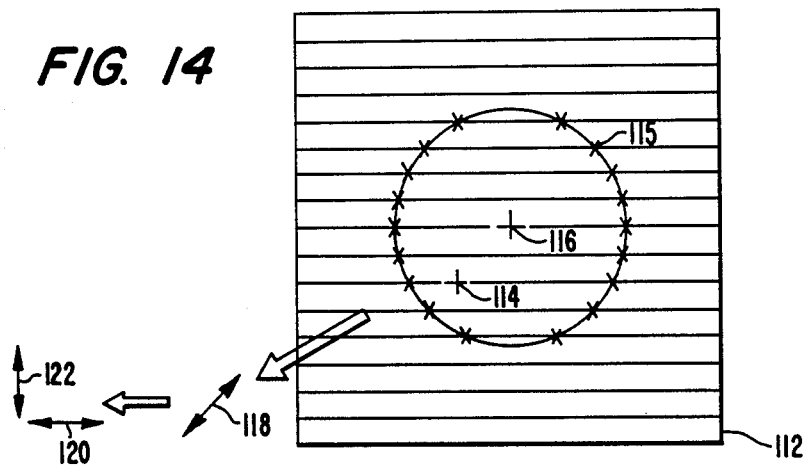
FIG. 14 is a further diagram representing the pupil-glint algorithm of x and y coordinates and showing determination.

With reference to FIG. 14, the region of interest 112 is scanned as to every pixel on both the x and y grid. This is best shown in the Figure where the horizontal line represents the scan of each pixel. The accumulated values of all x and y coordinates 115 at the perimeter of the pupil, that is, the end points of each horizontal chord divided by the total number of points is used to determine the x and y coordinate of the pupil center location 116. Also the brightest pixels in the region must be x and y coordinates of glint location 114. The difference between the x,y coordinates the center of the pupil 116 and the glint 114 are depicted at 118 showing the differential between the two and this is resolved at 120 showing the horizontal difference and 122 showing the vertical difference.

Figure 11:
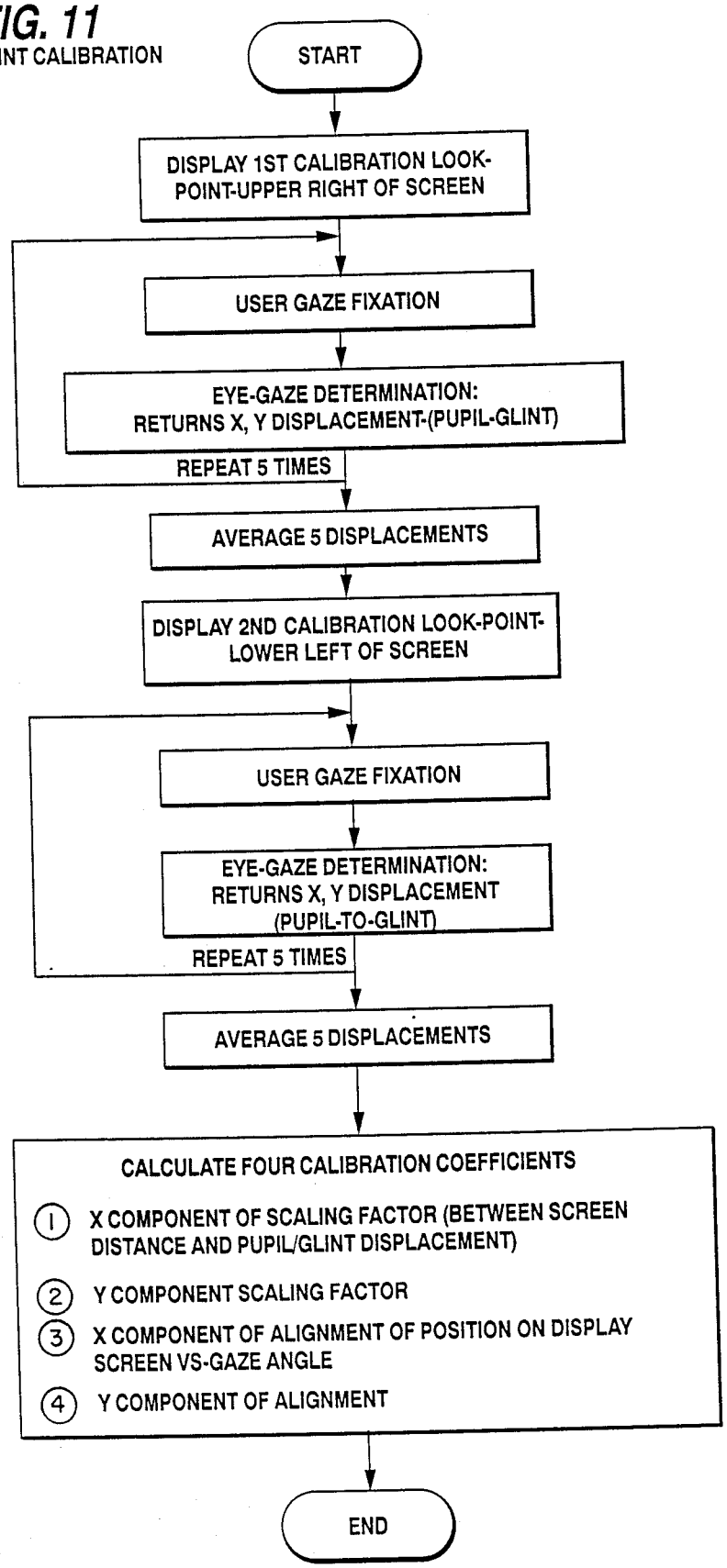
FIG. 11 is a flowchart relating to calibration of the eye movement detector.

With reference to FIG. 11 there is shown a flow chart relating to the calibration of the eye movement detector. The calibration technique uses two points. First, the first calibration look point icon is displayed in the upper right of the display screen and the user fixes his or her gaze on this icon. An eye gaze determination is made to show the x and y displacement between the center of the pupil and the glint when gazing at this first calibration look point. This is repeated five times for five different displacements which are averaged. Next a display of a second calibration look point icon is made at the lower left of the screen. The user fixes his or her gaze on this second calibration look point and an eye gaze determination returns the x,y displacement between the center of the pupil and the glint. This determination is repeated five times for an average of five displacements for the second calibration look point. From the average of the five displacements of the first calibration look point and the average of the five displacements for the second calibration look point, the following four calibration coefficients are calculated.

1. The x component of the scaling factor between the screen distance and the center of pupil and glint displacement.
2. The y component of the scaling factor between the screen distance and the center of pupil and glint displacement.
3. The x component of the alignment of position on display screen versus gaze angle.
4. The y component of the alignment of position on display screen versus the gaze angle.

And that completes the procedure for calibration.

The above calibration coefficients are referred to as the ax and ay or the x and y components of the scaling factor and bx and by, the alignment of position on the display screen versus the gaze angle.

With further reference to the calibration equations:
Relation between any gaze position and eye displacement vector is linear:

$$GAZE(x,y) = (+/-)A(x,y) * eye\_disp(x,y) + B(x,y)$$

where $(+)$ in the case of x, and $(-)$ in case of y, so that the gaze position is computed from eye displacement data knowing values of two coefficients A and B which depend both on eye characteristics such as size and corneal radius, and on relative positions of camera and subject. These coefficients are evaluated from eye displacement vectors measured during eye gaze at two screen positions.

Coefficient A is ratio of screen displacements to eye displacements:

$$A(x,y) = (SCREEN\_POS(right\_x, upper\_y) -$$
$$SCREEN\_POS(left\_x, lower\_y))/(eye\_disp(right\_x,$$
$$upper\_y) - eye\_disp(left\_x, lower\_y))$$

Coefficient B is an offset term to superpose screen coordinates onto the gaze look point:

$$B(x,y) = SCREEN\_POS(right\_x, upper\_y) - (A(x,y) * eye\_disp(right\_x, upper\_y))$$

For each of the above:
GAZE is a computed coordinate within the display screen,
SCREEN_POS is known screen coordinate of gaze calibration position 1 or 2,
eye-disp is measured vector between pupil center coordinate and glint coordinate,
A,B are coefficients determined from measurements of eye displacement.

Figure 12:
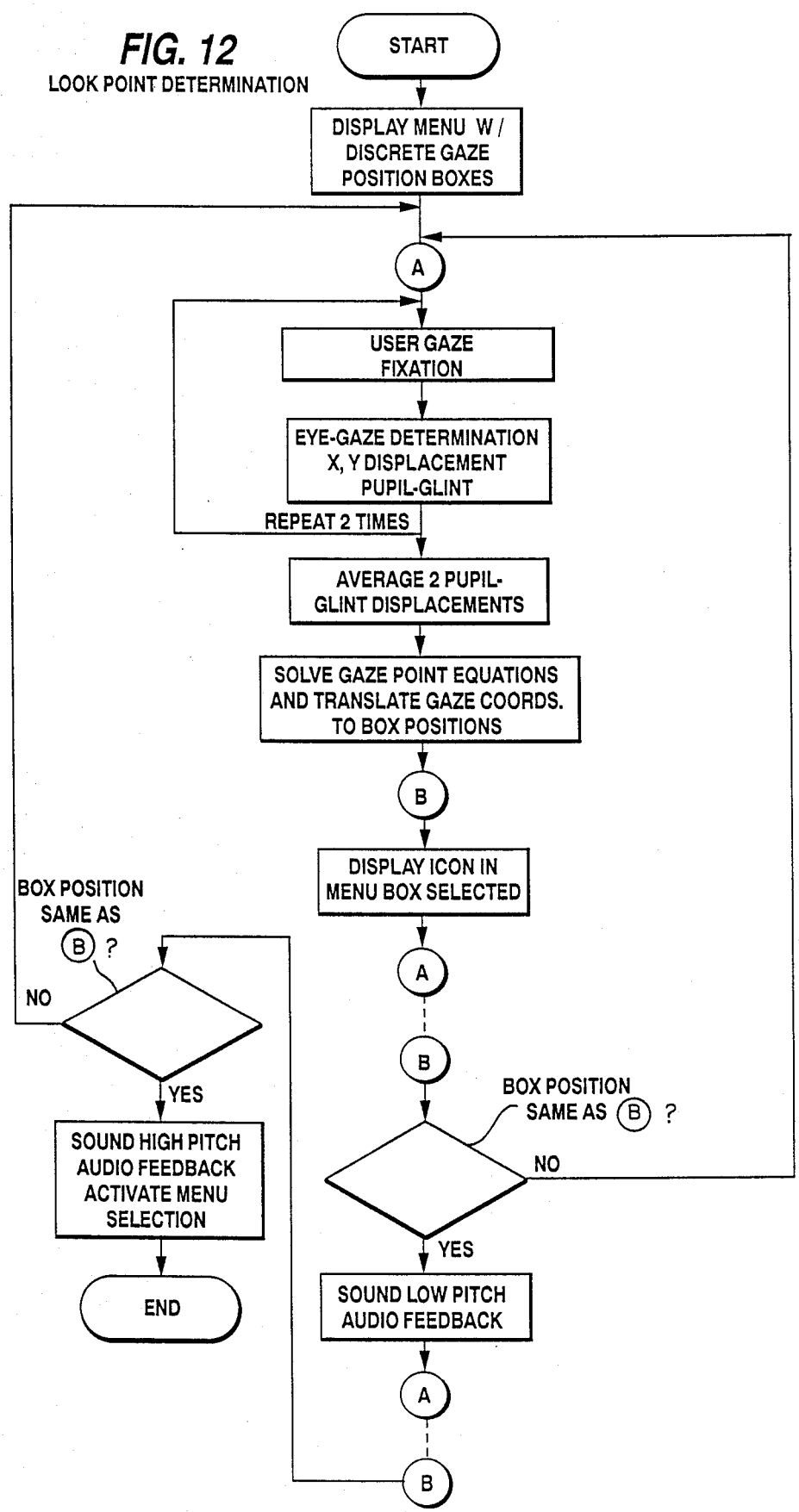
FIG. 12 is a flowchart relating to look point determination.

With reference to FIG. 12, there is shown a flow chart for the look point determination. This utilizes the calibration data and the current gaze to determine where the user is looking at the screen. It starts with the display menu that are at the present time in the form of little boxes 20 that are on the screen where the user would look. The user fixes his gaze on one of the boxes such as six different boxes shown in FIG. 1, holds it there for a sufficient time and the menu is actuated as to the box being viewed. The menu could be in the form of icons, letters of the alphabet and so forth but in all cases represent a discrete area of the display screen upon which the user views for a predetermined period of time to actuate that particular area.

FIG. 12 shows how this is done. The display menu is approached with discreet gaze position boxes. A first user gaze fixation is on a given area, a box on the screen. An eye gaze determination of x,y displacement between the center of the pupil and the glint is made. This is repeated two times and an average of the two pupil-glint displacements is made. The gaze point equations, which are the same as the calibration equations, are solved and translate gaze coordinates to the box positions. Then a display icon in the menu box selected is shown on the screen. At the present time the icon is an x insde a circle. This icon will appear any time that two pupil-glint displacements indicate a sufficient pause that the user may be looking at that part of the screen. The steps between "A" and "B" are repeated. If the box position is the same as "B" before a low pitch audio feed back sound is made by the computer. If the box position is not the same, then the entire procedure is started over. After the low pitch audio feedback is made, the steps in the flow chart between "A" and "B" are repeated and again if the box position is the same as "B" earlier then a high pitch audio feed back sound is made and the menu selected is activated. However, if the box position is not the same the procedure is aborted and the entire procedure starts again.

It is possible for the screen to show constantly where the eye is gazing but this is distracting to the user of the system as he or she has a tendency to look back to see where the eye has been. So instead the procedure is the that icon silently comes up after a pause is made for a little over a half second. In cases where it takes two seconds for the user to actuate a menu selection. Then one more frame grab will give a low beep and at that time the user can look away and abort the selection. The selection can also be aborted when the icon is first displayed by moving the eyes to another location. This arrangement takes six frame grabs while looking at the same area for the actuation to take place. Two for the first icon, four for the low pitch sound audio feed back and six four the high pitch sound and simultaneous actuator. And that is the end of the procedure.

Figure 15:
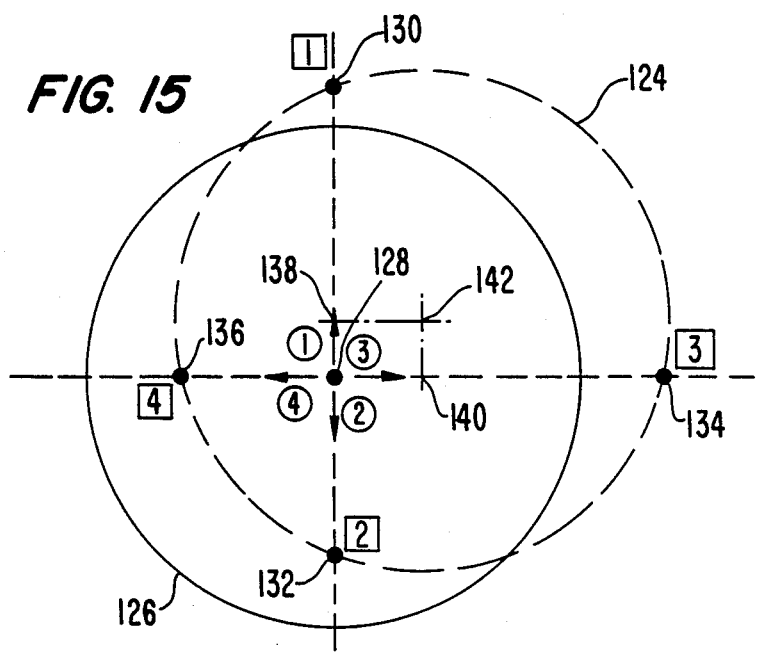
FIG. 15 is a diagram to show a fast search procedure.

With reference to FIG. 15, there is shown a procedure for fast searching of the eye gaze point. The dotted line circle 124 of FIG. 15 represents a new pupil position to be detected and the solid circle 126 represents the estimated prior pupil position from a prior frame that has been grabbed.

The fast search steps is to test if the center 128 from the prior frame 126 is within the new pupil position 124. If the answer is yes, then the fast search procedure can be utilized but if the answer is no, then the normal exhaustive search is performed as provided above. Assuming the center of the prior frame 128 is in the new pupil position 124, then the next step is to search up from the center 128 from the prior frame 126 to the edge of the new pupil 124 at 130 which, once found is position "1". Next, a search down from the center prior pupil 128 of the position 126 is made until the new pupil's 124 lower edge is intersected at 132 which is position "2".

Next a search is made to the right from the center 128 of the prior pupil position 126 until the right edge at 134 of the new pupil 124 is found. This is position "3". Next a search is made left from the center 128 of the prior pupil 126 until the left edge at 136 of the new pupil 124 is found which is position "4".

The next step is to make an estimate of the new vertical center 138 of the new pupil 124. This is the midpoint between position "1" at 130 and position "2" at 132. Next an estimate of the new horizontal center 140 of the new pupil 124 is made and that is the midway point between position "3" at 134 and position "4" at 136.

The new vertical center 138 and horizontal center 140 are used to give estimated center 142 of the new pupil. If the new estimated center 142 is within the pupil of the prior position 126 on both the x and y axis, then stop and utilized the new estimated center 142 as the actual center of the new pupil 124. Otherwise set this estimate of the center as a new starting point to repeat the relevant steps just outlined using the estimated center instead of the center 128 of the old pupil 126.

The concluding step is to locate the glint within the "screen region" of the new pupil by making an exhaustive search of each pixel of a square matrix region representing 1.2× the diameter of the new pupil and using the center of the pupil as the center of the matrix. With the fast determination of the location of the glint and the center of the pupil, the x,y displacement between the two enables a quick look point determination.

Figure 16A:
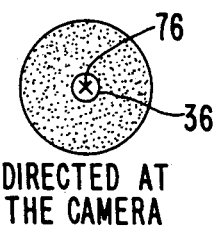
FIG. 16a shows the relative position of glint and center of pupil when eye look is directed at the videocamera.
Figure 16B:
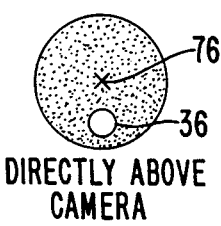
FIG. 16b shows the relative position of glint and center of pupil when eye look is directed above the videocamera.
Figure 16C:
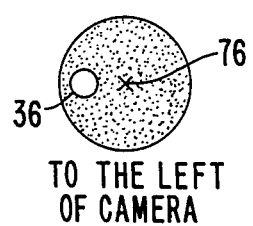
FIG. 16c shows the relative position of glint and center of pupil when eye look is directed to the left of the videocamera.
Figure 16D:
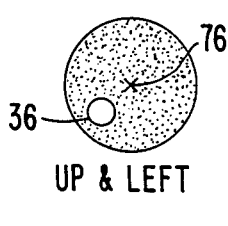
FIG. 16d shows the relative position of the glint and center of pupil when eye look is directed up and left of the videocamera.

With reference to FIGS. 16a through 16d, there is shown the relative location of the glint 36 and the center of the pupil 76 correlated with the gaze point. When the glint and pupil's center are centered as in FIG. 16a, the gaze point is directly into the camera. When the glint is directly below the pupil's center as in FIG. 16b, the gaze point is directly above the camera. When the glint is to the left of the pupil's center as seen from the camera in FIG. 16c, the gaze point is to the left of the camera as viewed from the operator's position. When the glint is below and to the left of the pupil's center as seen in FIG. 16d (as viewed from the camera), the gaze point is to the left and above the camera as viewed from the operator's position.

An eye motion detector and method has been described that provides a means by which a human operator, including a paraplegic, can interface directly with a computer by eye gaze alone in a relatively inexpensive, efficient, reliable, flexible and satisfactory manner. It is to be recognized that various other specific embodiments may be made of the invention and further changes may be incorporated in the device described and method set forth herein. And it is to be understood that all the material set forth or shown in the accompanying drawings is to be interpreted as illustrative and not in a limiting sense and that the invention is to be interpreted within the spirit and scope of the following claims.

What is claimed is:

1. An eye movement detector comprising:
   a display to be viewed by an operator;
   a camera with a lens located near said display and directed in a manner to obtain an image of an operator's eye when the display is being viewed;
   a small illuminator mounted in front of said camera lens and not further from the axis of said lens than one-half the distance from the center of said lens and the edge thereof and out of said lens' focus directed towards the position of an operator's eye so that the reflected illumination causes the operator's pupil to be brighter than the surrounding part of the eye due to the bright eye effect; and
   a computer for analyzing the image of an operator's eye to determine the center of the pupil and utilize said information to detect the eye position and correlate said position with whether or not the operator is gazing at the display.

2. The eye movement detector of claim 1, wherein there are multiple individual areas on the display representing different choices that can be made by an operator and said computer analysis determines at which individual area the operator is gazing.

3. The eye movement detector of claim 2, wherein said illuminator also causes a glint reflection from the cornea of the eye with said computer determining the gaze point by the displacement between the location of said glint and location of said center of the pupil relative to one another.

4. The eye movement detector of claim 3, wherein said illuminator is a near infrared light emitting semiconductor and said camera is sensitive to the near infrared wavelengths.

5. The eye movement detector of claim 4, wherein said infrared light emitting semiconductor is a gallium arsenide diode emitting light of a wavelength in the approximate range of 900 nanometers.

6. The eye movement detector of claim 4, wherein said computer analysis includes taking an image of the illuminated eye and placing it in a digitized matrix of pixels that is first analyzed by scanning a selected sampling of pixels, which may include every pixel or some lesser number of pixels, and determining with respect to each scanned pixel the light intensity value of the pixel and the frequency of occurrence of each pixel having the same intensity and making a determination of the pupil threshold by determining the minimum number of occurrences of pixel intensity of the same value between the pixel intensity represented by the pupil and the pixel intensity represented by the part of the eye and face surrounding the pupil.

7. The eye movement detector of claim 6, wherein the computer analysis further includes determining the glint threshold by finding the pixel intensity level between the maximum intensity of pixels representing the pupil and the minimum intensity of the pixels representing the glint.

8. The eye movement detector of claim 7, wherein said pupil-glint displacement is determined by first scanning the pixels in the matrix by a fine scan of the pixels in a given row and a rough scan of the number of rows to determine a first chord of predetermined length passing through the pupil image followed by determining the diameter of said pupil from a chord through the pupil at right angles to the midpoint of said first chord.

9. The eye movement detector of claim 8, wherein said fine scan is approximately every other pixel in a given row and said rough scan is approximately every 32 rows.

10. The eye movement detector of claim 9, wherein said computer creating a region of interest in said matrix that surrounds said pupil that is fractionally larger than said pupil with an approximate center of said region of interest being the midpoint of said pupil's diameter, said computer then re-scanning the entire region of interest at every pixel, using said re-scan information in calculating from said re-scan the location of said pupil's center and the location of said glint, then determining the pupil-glint displacement between said pupil center location and said glint location and from said pupil-glint displacement calculating the eye-gaze point.

11. The eye movement detector of claim 10, wherein said computer contains in its memory information representing each of said individual areas on the display, determining when said eye-gaze point has lingered on an individual area for greater than a predetermined interval of time and causing an action to take place when this occurs.

12. The eye movement detector of claim 11, wherein said computer determining a series of eye-gaze points and determining when said eye-gaze point lingers on an individual area longer than a predetermined first sub-interval of time and causing an icon to appear on said screen at said eye-gaze point.

13. The eye movement detector of claim 12, wherein said computer determining if said eye-gaze point remains unchanged for a second predetermined sub-interval of time and causing a first sound to be emitted when this occurs.

14. The eye movement detector of claim 13, wherein said computer determining if said eye-gaze point remains unchanging for a third predetermined sub-interval of time which in summary with said first and second sub-intervals equals a full interval of time and causing a second sound to be emitted and said action to take place when this occurs.

15. An eye movement detector comprising:

a display having multiple individual areas representing different choices that can be made by an operator when viewed by an operator for a predetermined interval of time;

a camera with a lens located near said display and directed in a manner to obtain an image of an operator's eye when the display is being viewed;

an illuminator directing an infrared source of illumination coaxial with said camera lens towards the position of an operator's eye so that the reflected illumination causes the operator's pupil to be brighter than the surrounding part of the eye due to the bright eye effect and also causes a glint reflection from the cornea of the eye;

a computer for analyzing said image of an illuminated operator's eye to determine the center of the pupil and location of the glint and utilizing said information in determining the eye-gaze point and correlating said eye-gaze point with whether or not the operator is gazing at an individual area of the display; and said computer analysis including using said image of the operator's eye in a digitized matrix of pixels that is first analyzed by scanning a selected sampling of pixels, which may include every pixel or some lesser number of pixels, and determining with respect to each scanned pixel the light intensity value of the pixel and the frequency of occurrence of each pixel having the same intensity and making a determination of the pupil intensity threshold by determining the minimum number of occurrences of pixel intensity of the same value between the pixel intensity represented by the pupil and the pixel intensity represented by the part of the eye and face surrounding the pupil and also determining the glint intensity threshold by finding the pixel intensity level between the maximum intensity of pixels representing the pupil and the minimum intensity of the pixels representing the glint.

16. The eye movement detector of claim 15, wherein said eye-gaze point is determined by utilizing said pupil threshold and said glint threshold by the computer first scanning the pixels in said matrix by a fine scan of the pixels in a given row and a rough scan of the number of rows to determine a first chord of predetermined length passing through the pupil image followed by determining the diameter of said pupil from a chord through the pupil at right angles to the midpoint of said first chord.

17. The eye movement detector of claim 16, wherein said fine scan is approximately every other pixel in a given row and said rough scan is approximately every 32 rows.

18. The eye movement detector of claim 17, wherein said computer creating a region of interest in said matrix that surrounds said pupil that is fractionally larger than said pupil with an approximate center of said region of interest being the midpoint of said pupil's diameter, said computer then re-scanning the entire region of interest at every pixel, using said re-scan information in calculating from said re-scan the location of said pupil's center and the location of said glint, then determining the pupil-glint displacement between said pupil center location and said glint location and from said pupil-glint displacement calculating said eye-gaze point.

19. The eye movement detector of claim 18, wherein said computer contains in its memory information representing each of said individual areas on the display, determining when said eye-gaze point has lingered on an individual area for greater than a predetermined interval of time and causing an action to take place when this occurs.

20. The eye movement detector of claim 19, wherein said computer determining a series of eye-gaze points and determining when said eye-gaze point lingers on an individual area longer than a predetermined first sub-interval of time and causing an icon to appear on said screen at said eye-gaze point.

21. The eye movement detector of claim 20, wherein said computer determining if said eye-gaze point remains unchanged for a second predetermined sub-interval of time and causing a first sound to be emitted when this occurs.

22. The eye movement detector of claim 21, wherein said computer determining if said eye-gaze point remains unchanging for a third predetermined sub-interval of time which in summary with said first and second sub-intervals equals a full interval of time and causing a second sound to be emitted and said action to take place when this occurs.

23. The eye movement detector of claim 19 wherein after determining an eye-gaze point, rapidly determining subsequent eye-gaze points by said computer determining if the prior pupil center of the prior gaze point is within the new pupil and, if so, utilizing the prior pupil center to erect vertical and horizontal chords through the said new pupil, utilizing said chords in determining an estimate of said new pupil center and if said estimated new pupil center is within said prior pupil, utilizing said estimated new pupil center as the actual new pupil center.

24. A method for determining eye-gaze comprising the follows steps:
placing on a display multiple individual areas representing different choices that can be made by an operator when viewed by an operator for a predetermined interval of time;
obtain an image of an operator's eye by a camera with a lens located near the display and when the display is being viewed;
illuminate the operator's eye by directing an infrared source of illumination coaxial with said camera lens towards the position of an operator's eye so that the reflected illumination causes the operator's pupil to be brighter than the surrounding part of the eye due to the bright eye effect and also causes a glint reflection from the cornea of the eye;
analyze said image of the operator's eye to determine the center of the pupil and location of the glint and utilize said information to determine the eye-gaze point and correlate said eye-gaze point with whether or not the operator is gazing at an individual area of the display; and
using said image of the operator's eye to produce a digitized matrix of pixels that is first analyzed by scanning a selected sampling of pixels, which may include every pixel or some lesser number of pixels, and determine with respect to each scanned pixel the light intensity value of the pixel and the frequency of occurrence of each pixel having the same intensity and make a determination of the pupil intensity threshold by determining the minimum number of occurrences of pixel intensity of the same value between the pixel intensity represented by the pupil and the pixel intensity represented by the part of the eye and face surrounding the pupil and also determine the glint intensity threshold by finding the pixel intensity level between the maximum intensity of pixels representing the pupil and the minimum intensity of the pixels representing the glint.

25. The method of determining eye-gaze of claim 24, including first scanning the pixels in the matrix by a fine scan of the pixels in a given row and a rough scan of the number of rows to determine a first chord of predetermined length passing through the pupil image followed by determining the diameter of said pupil from a chord through the pupil at right angles to the midpoint of said first chord.

26. The method of determining eye-gaze of claim 25, including creating a region of interest in the matrix that surrounds the pupil that is fractionally larger than the pupil with an approximate center of said region of interest being the midpoint of said pupil's diameter, then re-scanning the entire region of interest at every pixel, calculate from said re-scan information the location of said pupil's center and the location of said glint, then determine the pupil-glint displacement between said pupil center location and said glint location and from said pupil-glint displacement calculate the eye-gaze point.

27. The method of using as a computer interface the eye gaze determination of claim 26, including placing in the computer memory information representing each of the individual areas on the display, determine when said eye-gaze point has lingered on an individual area for greater than a predetermined interval of time and cause an action to take place when this occurs.

28. The method of using eye-gaze as a computer interface of claim 27, including determining a series of eye-gaze points and determine when the eye-gaze lingers on an individual area longer than a predetermined first sub-interval of time and cause an icon to appear on said screen at said eye-gaze point.

29. The method of using eye-gaze as a computer interface of claim 28, including determining if said eye-gaze point remains unchanged for a second predetermined sub-interval of time, cause a first sound to be emitted when this occurs and determine if said eye-gaze point remains unchanging for a third predetermined sub-interval of time which in summary with said first and second sub-intervals equals a full interval of time and cause a second sound to be emitted and said action to take place when this occurs.

30. The method of determining eye-gaze of claim 24 including the steps of determine subsequent eye-gaze points rapidly by first making a determination of whether the prior pupil center of the prior gaze point is within the new pupil and, if so, utilize the prior pupil center to erect vertical and horizontal chords through the new pupil then utilize said chords to determine an estimate of the new pupil center and, if said estimated new pupil center is within said prior pupil, utilize said estimated new pupil center as the actual new pupil center.

31. For use in an eye movement detector, a camera lens and illuminator subassembly comprising:

a solid state infrared sensitive camera with a lens for use in obtaining an image of an operator's eye;

a small infrared illuminator mounted coaxially with and in the center and front of said camera lens; and said illuminator having a lens to form and direct the infrared radiation outward from the front of said camera lens.

* * * * *